United States Patent
Friedman

Patent Number: 6,059,768
Date of Patent: *May 9, 2000

[54] CODED INTRAVENOUS TUBING

[76] Inventor: David J. Friedman, 2124 Pembroke Dr., Fort Worth, Tex. 76110

[*] Notice: This patent issued on a continued prosecution application filed under 37 CFR 1.53(d), and is subject to the twenty year patent term provisions of 35 U.S.C. 154(a)(2).

[21] Appl. No.: 09/130,257

[22] Filed: Aug. 6, 1998

Related U.S. Application Data

[60] Provisional application No. 60/055,393, Aug. 6, 1997.

[51] Int. Cl.⁷ .................................................. A61M 5/00
[52] U.S. Cl. .......................................... 604/523; 604/264
[58] Field of Search .................. 604/49, 52, 53, 604/264, 280, 282, 116, 80, 523, 525, 526, 529

[56] References Cited

U.S. PATENT DOCUMENTS

| | | | |
|---|---|---|---|
| 2,896,619 | 7/1959 | Bellamy, Jr. | 604/409 |
| 3,495,595 | 2/1970 | Soper | 604/28 |
| 3,932,869 | 1/1976 | Kane . | |
| 3,987,438 | 10/1976 | Lindenmueller et al. . | |
| 4,447,239 | 5/1984 | Krutten | 604/282 |
| 4,586,904 | 5/1986 | Chlumsky . | |
| 4,654,026 | 3/1987 | Underwood | 604/80 |
| 4,709,499 | 12/1987 | Ottaviano | 43/17.6 |
| 4,735,516 | 4/1988 | Galarneau . | |
| 4,823,497 | 4/1989 | Pierce | 43/17.6 |
| 4,859,094 | 8/1989 | Okada . | |
| 4,900,314 | 2/1990 | Quackenbush . | |
| 5,116,310 | 5/1992 | Seder et al. | 604/43 |
| 5,236,417 | 8/1993 | Wallis | 604/82 |
| 5,279,280 | 1/1994 | Bacich et al. | 128/6 |
| 5,342,301 | 8/1994 | Saab | 604/96 |
| 5,364,352 | 11/1994 | Cimino et al. | 604/95 |
| 5,423,750 | 6/1995 | Spiller | 604/80 |
| 5,487,731 | 1/1996 | Denton | 604/100 |

OTHER PUBLICATIONS

Webster's II, New Riverside University Dictionary, p. 224, 1984.

Sherwood Product Catalogue, THI Aortic Perfusion Cannulae, p. 1 and Sherwood Medical: A Commitment to Leadership and Innovation, p. 1, Jul. 19, 1990.

*Primary Examiner*—Wynn Wood Coggins
*Assistant Examiner*—LoAn H. Thanh
*Attorney, Agent, or Firm*—Felsman Bradley Vaden Gunter & Dillon, LLP; James E. Bradley

[57] ABSTRACT

Tubing for use with intravenous delivery of fluids to a patient is provided. The tubing is preferably see-through and includes a tubing wall defining an exterior surface and an interior surface. The interior and exterior wall surfaces define a channel for transferring intravenous fluid. An indicator for visibly distinguishing one tube from another similar tube is provided. The visible indicator may be a protruding ridge or a depression that traverses a length of the exterior surface, wherein the protruding ridge is helically wrapped around the exterior surface or run down a length of the tube longitudinally. The indicator may have a rectangular cross section, a hemispherical cross section or other suitable shape that traverses a length of the exterior surface. The indicator may additionally be colored or chemiluminescent to make the indicator more visible.

3 Claims, 2 Drawing Sheets

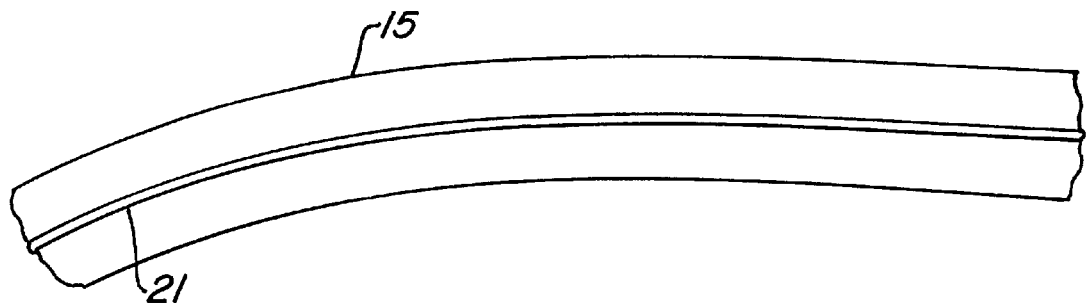
Fig. 5
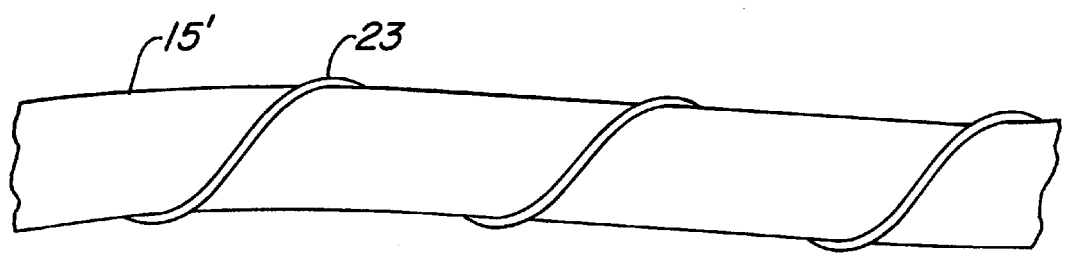
Fig. 6
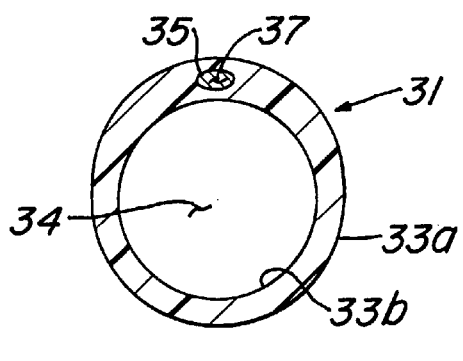 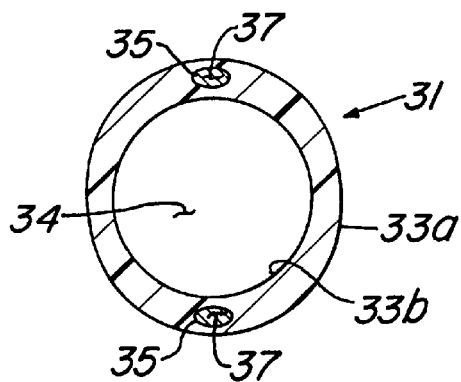
Fig. 7        Fig. 8

CODED INTRAVENOUS TUBING

CROSS-REFERENCE TO RELATED APPLICATIONS

This application claims the benefit of provisional application No. 60/055,393, filed Aug. 6, 1997.

TECHNICAL FIELD

This invention relates to tubing for use with intravenous delivery of fluids to a patient. More specifically, the invention relates to a coding or identification means for intravenous tubing.

BACKGROUND ART

It is common in the medical industry for patients to simultaneously receive multiple intravenous medication solutions through intravenous tubing that is coupled together and inserted into the patient's veins or arteries at one or more sites on the body either via peripheral or central venous catheters. The multiple intravenous tubes are long and transparent and frequently become entangled, intertwined or twisted, making it difficult for medical personnel to determine which medication is flowing through which intravenous tube. Although problematic in a wide variety of clinical situations this is particularly so in desperately ill patients, such as in an intensive care setting, where patients have multiple peripheral and/or central lines containing a variety of high risk medications and possible incompatible solutions. It is also important during simple or complex anesthesia when patients are covered and the orientation of their intravenous lines has changed because of patient positioning (for example from supine to prone) and subsequent draping of various parts of their bodies. Another example would be in oncology, where many of the chemotherapy drugs have strictly defined compatibility ranges with other solutions and medications. All these lines are connected to multiple infusion pumps programmed to infuse each solution or medication at an appropriate and safe rate. Additional doses of medications have to be injected or infused at multiple times during the day through separate lines, all of which are transparent and look the same.

The complexity of this problem is compounded by staff shift changes, and, thereby, patient care delivered by different nursing personnel two to three times a day. Each time the nurses have to orient themselves to the various lines, solutions and different medications for each patient under their care. When there is a sudden change in a patient's condition, rapid line content recognition and use becomes a necessity during the emergency. These times are often handled by personnel unfamiliar with the patient.

Nurses often tag the multiple lines leading to a patient in an attempt to circumvent these problems, but this only provides identification of the line close to the tag and entangled lines must still be followed from the tag and disentangled for identification prior to use.

The development of lines with a structural marker along the entire length would offer distinct advantages over other methods of line identification. If the structural change included a chemiluminescent material, this would not only add color, but also enhanced visibility at night. A situation can be conceived that all patients in a particular clinical discipline who require a certain high risk solution will receive it in a specifically coded intravenous tubing. This would facilitate immediate recognition of the nature of the medication by all members of staff, regardless of whether or not they are directly involved in the care of the patient.

Finally, apart from the obvious safety advantages of intravenous tubing coded in this way, depending upon the nature of mode of the structural change and the type of color or chemiluminescent material added, these types of intravenous tubes would be far less threatening and possibly entertaining to children or very young patients.

Therefore it is desirable to provide intravenous tubing having an indicator for visibly distinguishing one intravenous tube from another intravenous tube. Electrical wiring is manufactured in various colors and color combinations for identification purposes. Additionally, coding bands have been used for identifying or coding electrical cables. However, no clear plastic intravenous tubing is available with any identification means present over a length of tubing for distinguishing one tube from another tube.

DISCLOSURE OF INVENTION

Tubing for use with intravenous delivery of fluids to a patient is provided. The tubing may be either transparent or translucent. The tubing includes a tubing wall, which defines an exterior surface and an interior surface. The interior surface defines a channel for transferring intravenous fluid. A visible indicator is provided for visibly distinguishing one tube from another similar tube. The visible indicator may be a protruding ridge that traverses a length of the exterior surface. The protruding ridge may be integral with the tube or affixed thereto. The protruding ridge may be helically wrapped around the exterior surface or run down a length of the tube longitudinally. The indicator may have a rectangular cross section, a hemispherical cross section or other suitable shape. Additionally, the indicator may be a groove in the exterior surface or embedded within the tubing. The indicator may further be colored or chemiluminescent to make the indicator more visible. More than one indicator may be added to the tube. The multiple indicators may be the same or different and be placed in an equidistant or unequal distance from each other on the tube.

DESCRIPTION OF THE DRAWINGS

FIG. 5 is a side elevational view of the coded intravenous tubing of FIG. 3 shown with the coding means running longitudinally along the coded intravenous tubing.

FIG. 6 is a side elevational view of the coded intravenous tubing of FIG. 3 shown with the coding means running helically around the coded intravenous tubing.

FIG. 7 is a cross-sectional view of another alternate embodiment of the coded intravenous tubing of the present invention.

FIG. 8 is a cross-sectional view of another alternate embodiment of the coded intravenous tubing of the present invention.

BEST MODE OF THE INVENTION

Figure 1:
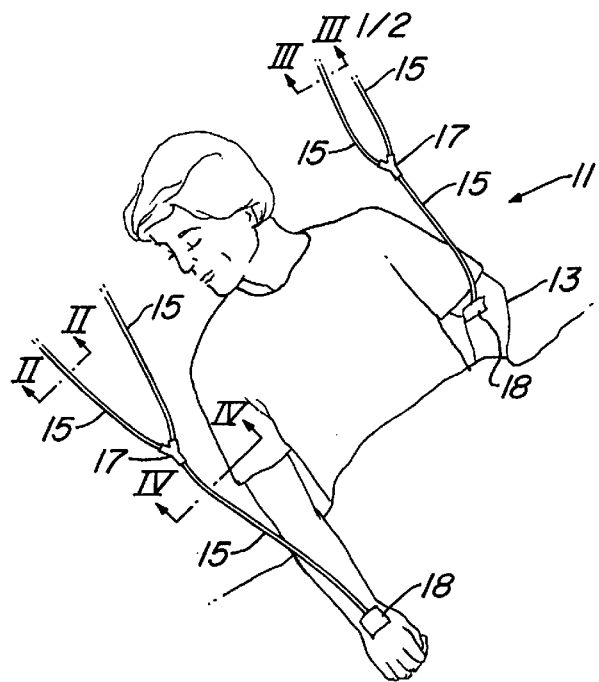
FIG. 1 is a perspective view of a patient being administered intravenous medication through coded intravenous tubes of the present invention.

Referring to FIG. 1 in the drawings, numeral 11 illustrates the preferred embodiment of the coded intravenous tubing of the present invention. A patient 13 is shown simultaneously receiving multiple intravenous medications (not shown) through a plurality of coded intravenous tubes 15. Coded intravenous tubing 15 is preferably made of pliable plastic or nylon, as is conventional, and can be used in place of conventional intravenous tubing. Typically, intravenous tubing is transparent. A plurality of conventional intravenous tubing couplers 17 are shown coupling a plurality of coded intravenous tubes 15 together. It is common in the medical industry to couple multiple intravenous tubes together so that patient 13 may simultaneously receive multiple intravenous medications through the minimum number of intravenous sites 18.

Figure 2:
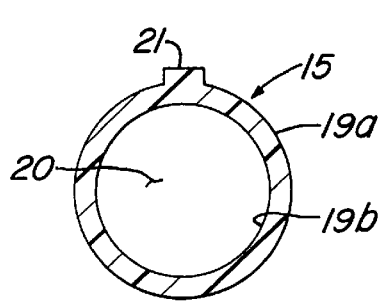
FIG. 2 is a cross-sectional view of the preferred embodiment of the coded intravenous tubing of the present invention taken at II—II of FIG. 1.

Referring now to FIG. 2 in the drawings, a cross-sectional view of the preferred embodiment of coded intravenous tubing 15 is shown. Coded intravenous tubing 15 is generally tubular in cross-section with tubing wall 22 defining an exterior surface 19*a* and an interior surface 19*b*. Interior surface 19*b* defines a channel 20 that is generally circular in cross-section and through which flows intravenous medication. Coded intravenous tubing 15 has at least one coding rib 21 that protrudes radially from exterior surface 19*a* and extends the length of tubing 15. Coding rib 21 may be integrally manufactured with coded intravenous tubing 15, or coding rib 21 may be coupled to coded intravenous tubing 15 after coded intravenous tubing 15 is manufactured. Coding rib 21 may encode intravenous tubing 15 as a single rib or multiple ribs. Coding rib 21 is generally rectangular in cross-section and may be manufactured in various dimensions and colors and may or may not comprise chemiluminescent material. Coding rib 21 allows medical personnel to quickly and accurately determine which intravenous medication is flowing through which coded intravenous tube 15 as described above.

Figure 3:
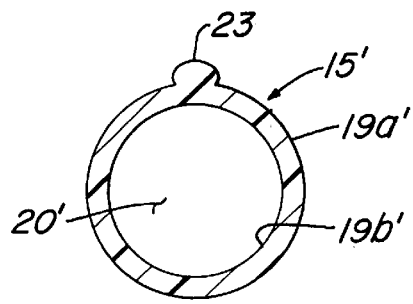
FIG. 3 is a cross-sectional view of an alternate embodiment of the coded intravenous tubing of the present invention taken at II—II of FIG. 1.

Referring now to FIG. 3 in the drawings, a cross-sectional view of an alternate embodiment of coded intravenous tubing 15 is shown. Coded intravenous tubing 15' is generally tubular in cross-section with tubing wall 24 defining an exterior surface 19*a*' and an interior surface 19*b*'. Interior surface 19*b*' defines a channel 20' that is generally circular in cross-section and through which flows intravenous medication. Coded intravenous tubing 15' has at least one coding rib 23 that protrudes radially from exterior surface 19*a*' and extend continuously along the length of tubing 15'. Coding rib 23 may be integrally manufactured with coded intravenous tubing 15', or coding rib 23 may be coupled to coded intravenous tubing 15' after coded intravenous tubing 15' is manufactured. Coding rib 23 is generally hemispherical in cross-section and may be manufactured in various dimensions and colors and may or may not comprise chemiluminescent material. Coding rib 23 allows medical personnel to quickly and accurately determine which intravenous medication is flowing through which coded intravenous tube 15' as described above.

Figure 4:
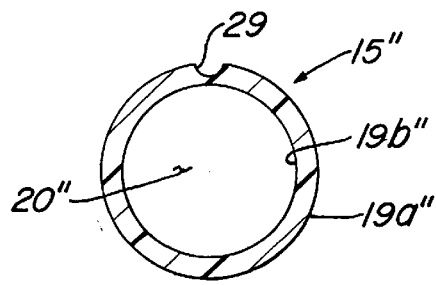
FIG. 4 is a cross-sectional view of another alternate embodiment of the coded intravenous tubing of the present invention taken at IV—IV of FIG. 1.

Referring now to FIG. 4 in the drawings, a cross-sectional view of another alternate embodiment of coded intravenous tubing 15 is shown. Coded intravenous tubing 15" is generally tubular in cross-section with tubing wall 25 defining an exterior surface 19*a*" and an interior surface 19*b*". Interior surface 19*b*" defines a channel 20" that is generally circular in cross-section and through which flows intravenous medication. Coded intravenous tubing 15" has at least one coding groove 29 that intrudes radially inward from exterior surface 19*a*" and extends along the length of tubing 15'. The tubing wall will need to be slightly thicker to safely accommodate the grooves along its length. Coding groove 29 may be integrally manufactured with coded intravenous tubing 15", or coding groove 29 may be created by a conventional grooving process after coded intravenous tubing 15" is manufactured. Coding groove 29 is generally hemispherical in cross-section and may be manufactured in various dimensions and colors or coated with a chemiluminescent material. Coding groove 29 allows medical personnel to quickly and accurately determine which intravenous medication is flowing through which coded intravenous tube 15" as described above.

Referring now to FIG. 5, at least one coding rib 21 or 23 (see FIG. 2) runs longitudinally along coded intravenous tubing 15 parallel to the axis of tubing 15. It is understood that coding rib 23 (see FIG. 3) and groove 29 (see FIG. 4) may be located on intravenous tubing 15' and 15", respectively, in this same longitudinal fashion. Moreover, more than one of the ribs 21, 23 or grooves 29 could be located on the same tubing 15 either equidistantly or unevenly placed along the tube. Tubing 15 could also contain a combination of ribs 21, 23 and groove 29.

Referring now to FIG. 6, at least one coding rib 23 (see FIG. 3) wraps helically around coded intravenous tubing 15'. It is understood that coding rib 21 (see FIG. 2) and groove 29 (see FIG. 4) may be located on coded intravenous tubing 15 and 15", respectively, in this same helical fashion.

Referring now to FIG. 7 and FIG. 8 in the drawings, a cross-sectional view of another alternate embodiment of the present invention is shown. Coded intravenous tubing 31 is generally tubular in cross-section with tubing wall 32 defining an exterior surface 33*a* and an interior surface 33*b*. Interior surface 33*b* defines a channel 34 that is generally circular in cross-section and through which flows intravenous medication. Located between exterior surface 33*a* and interior surface 33*b* is a coding passage or channel 35. Coding channel 35 is preferably circular or elliptical in cross-section. At least one color coating substance 37 is carried within coding channel 35. Preferably, the coating substance 37 may be a chemiluminescent material which glows in the dark. Coding channel 35 is preferably integrally manufactured with coded intravenous tubing 31. Coating substance 37 may be integrally manufactured with coded intravenous tubing 31 and coding channel 35, or it may be inserted into coding channel 35 after coded intravenous tubing 31 is manufactured. Coating substance 37 may be manufactured in various colors. Coating substance 37 allows medical personnel to quickly and accurately determine which intravenous medication is flowing through which coded intravenous tube 31 as described above. Referring to FIG. 8 in the drawings, the coded intravenous tubing of FIG. 7 is shown with two coding channels 35 and two corresponding coating substance 37. It should be appreciated that coding ribs 21 and 23 may also be formed of a conventional chemiluminescent material such as the type that glows in the dark when activated. If coding ribs 21 and 23 or substance 37 is chemiluminescent, then it may be used to either indicate which medication is flowing through coded intravenous tubing 15, 15', or 31, respectively; or it may be used to entertain patients 13, especially when the patient 15 is a young child being administered intravenous medication. In the case of children, a different substance can be inserted in place of chemiluminescent material for possible entertainment purposes.

It should be apparent from the foregoing that an invention having significant advantages has been provided. The ribs, grooves, and channels provide recognizable characteristics for physicians and nurses, making it easier to trace particular tubes from the pump to the patient. The ribs and grooves can be felt in the dark to identify tubes by touch, even if not chemiluminescent. The ribs, grooves, and channels provide medical personnel the ability to readily assign the administration of high risk solutions, such as chemotherapy, cardiac drugs, etc., through immediately recognizable lines. The readily distinguishable lines will prevent the mixing of incompatible solutions within tubing, help prevent errors by health-care personnel and facilitate overall patient management.

While the invention is shown in only one of its forms, it is not so limited but is susceptible to various changes and modifications without departing from the spirit thereof.

I claim:

1. An intravenous tubing, comprising:

a cylindrical tubing wall having an axis, an exterior surface, and an interior surface which defines a passage for transporting intravenous fluid, wherein the fluid may be visually observed through the tubing wall; and a cavity extending continuously along substantially an entire length of the tubing wall for visually distinguishing the tubing, the passage being sealed from the cavity by the tubing wall; and wherein the cavity is filled with a chemiluminescent material.

2. The tubing of claim 1, wherein the cavity extends continuously along an entire length of the tubing wall between the exterior surface and the interior surface.

3. The tubing of claim 1, wherein the cavity extends continuously along one side of the tubing wall between the exterior surface and the interior surface and has an axis parallel and offset from the axis of the tubing wall.

* * * * *